United States Patent [19]
Dixson et al.

[11] Patent Number: 5,149,357
[45] Date of Patent: Sep. 22, 1992

[54] HERBICIDAL SUBSTITUTED BENZOYLSULFONAMIDES

[75] Inventors: John A. Dixson, Newtown, Pa.; Natesan Murugesan, Lawrenceville, N.J.; Keith D. Barnes, Newtown, Pa.

[73] Assignee: FMC Corporation, Philadelphia, Pa.

[21] Appl. No.: 540,653

[22] Filed: Jun. 19, 1990

[51] Int. Cl.$^5$ .................. A01N 43/54; C07D 239/60; C07D 417/10; C07D 413/10
[52] U.S. Cl. .................................. 71/92; 71/90; 71/93; 544/216; 544/238; 544/295; 544/300; 544/301; 544/310; 544/311; 544/312; 544/316; 544/321; 544/323; 544/324; 544/327; 544/331; 544/332
[58] Field of Search ............... 544/216, 238, 295, 296, 544/300, 301, 310, 311, 312, 316, 321, 323, 324, 327, 331, 332; 71/90, 92, 93

[56] References Cited

U.S. PATENT DOCUMENTS

| | | | |
|---|---|---|---|
| 4,770,691 | 9/1988 | Nezu et al. | 71/92 |
| 4,871,387 | 10/1989 | Sasse et al. | 544/316 |
| 5,057,143 | 10/1991 | Rheinheimer et al. | 71/92 |

FOREIGN PATENT DOCUMENTS

| | | |
|---|---|---|
| 0287079 | 6/1988 | European Pat. Off. . |
| 3820484 | 6/1988 | Fed. Rep. of Germany . |

Primary Examiner—Patricia L. Morris
Attorney, Agent, or Firm—Norman L. Craig; Robert M. Kennedy

[57] ABSTRACT

Compound of the formula

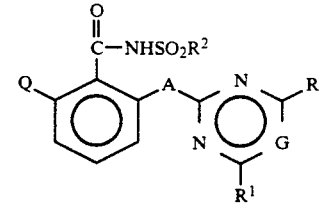

in which A is O, S, or $NR^3$; G is CH or N; R and $R^1$ are independently alkyl, alkoxy, haloalkoxy or alkylamino; $R^2$ is phenyl, substituted phenyl, alkyl, cycloalkyl, haloalkyl or $-CH_2[(R^4)C(R^5)_n-Z$; $R^3$ and $R^7$ are, independently, hydrogen, alkyl, $-C(O)NH_2$ or $-C(O)$alkyl; $R^4$ and $R^5$ are independently hydrogen, alkyl, or halogen; $R^6$ is halogen, alkyl, alkoxy, haloalkoxy, $NO_2$, amino, alkyl substituted amino, or acyl substituted amino; n is 0 to 5; Z is cyano, amino, alkylamino, dialkylamino, $-NHCO_2$alkyl, alkoxy, alkylthio, alkylsulfonyl, alkenyl, alkynyl, phenyl or substituted phenyl; and Q is hydrogen, halogen, alkyl, alkoxy, haloalkoxy, nitro, amino, haloalkyl, alkythio, alkylsulfonyl, phenyl, substituted phenyl or phenoxy; or a 5 or 6 membered aromatic heterocycle having the formula

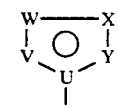

OR

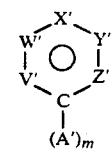

in which "m" is 0 or 1; A' is O, S, or $NR^7$; and X, X', Y, Y', W, W', V, V', U and Z' are independently N, O, S, $-CH-$ or $-CR^6$. Intermediates for preparation of the benzoylsulfonamides are also disclosed.

17 Claims, No Drawings

HERBICIDAL SUBSTITUTED BENZOYLSULFONAMIDES

This application pertains to weed control in agriculture, horticulture, and other fields where there is a desire to control unwanted plant growth. More specifically, the present application describes novel herbicidal 6-optionally substituted-2-substituted benzoylsulfonamides, compositions of them, methods of preparing them, and methods for controlling undesired plant growth by preemergence or postemergence application of the herbicidal compositions to the locus where control is desired. The present compounds may be used to effectively control a variety of both grassy and broadleaf plant species.

This invention relates to herbicidal compounds of the formula:

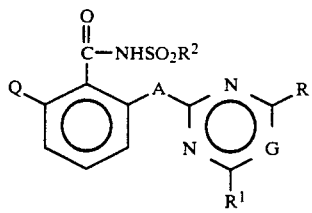

in which
A is O, S, or —N—$R^3$ in which $R^3$ is hydrogen, alkyl (e.g. methyl or ethyl), —C(O)NH$_2$, or —C(O)-alkyl (e.g. —C(O)—CH$_3$).
G is —CH— or —N—;
R and $R^1$ are independently alkyl (e.g. methyl), alkoxy (e.g. methoxy), haloalkoxy (e.g. —OCHF$_2$ or —OCH$_2$CH$_2$Cl), or alkylamino (e.g. —NHCH$_3$ or —N(CH$_3$)$_2$).
$R^2$ is lower alkyl, cycloalkyl, haloalkyl, phenyl, substituted phenyl or —CH$_2$[(R$^4$)C(R$^5$)]$_n$—Z in which $R^4$ and $R^5$ are independently hydrogen, alkyl or halogen; n is 0 to 5; and Z is cyano, amino, alkylamino, dialkylamino, —NHCO$_2$alkyl, alkoxy, alkylthio, alkylsulfonyl, alkenyl, alkynyl, phenyl or substituted phenyl.

In one aspect of the invention, Q is hydrogen, halogen, alkyl, alkoxy, haloalkoxy, nitro, amino, haloalkyl, alkylthio, alkylsulfonyl, phenyl, substituted phenyl, phenoxy or substituted phenoxy.

In another aspect of the invention, Q is a 5- or 6-membered aromatic heterocyclic ring selected from thiophene, furan, pyrrole, pyrazole, isoxazole, isothiazole, imidazole, oxazole, thiazole, oxadiazole, thiadiazole, triazole, tetrazole, pyridine, pyrimidine, pyrazine, pyridazine and triazine; and having the formula

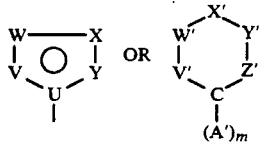

Formula II in which
"m" is 0 or 1;
A' is oxygen, sulfur or NR$^7$ in which R$^7$ is hydrogen, alkyl (e.g. methyl or ethyl), —C(O)NH$_2$ or —C(O)-alkyl (e.g. —C(O)—CH$_3$); and U, V, V', W, W', X, X', Y', Y and Z' are independently nitrogen, oxygen, sulfur, —CH— or —CR$^6$ in which R$^6$ is halogen (e.g. chlorine or fluorine), lower alkyl (e.g. methyl or isopropyl), lower alkoxy (e.g. methoxy), lower haloalkoxy (e.g. difluoromethoxy), NO$_2$, amino, alkyl substituted amino in which the alkyl group has 1-4 carbon atoms (e.g. —NHCH$_3$, —N(CH$_3$)$_2$), acyl substituted amino

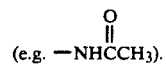

For substituted phenyl and phenoxy mentioned above, the substituents may be, for instance, halogen (e.g. chlorine and fluorine), lower alkyl (e.g. methyl), lower alkoxy (e.g. methoxy), nitro, amino, lower haloalkyl (e.g. trifluoromethyl or difluoromethyl), lower haloalkoxy (e.g. trifluoromethoxy or difluoromethoxy), lower alkylthio (e.g. methylthio), lower alkylsulfonyl (e.g. methylsulfonyl), lower alkenyl (e.g. vinyl or 1-propenyl), lower alkynyl (e.g. ethynyl or propargyl), lower alkenyloxy (e.g. 2-propenyloxy) or lower alkynyloxy (e.g. propargyloxy), or two substituents taken together to form a C$_1$–C$_3$ alkylenedioxy heterocyclic ring (e.g. benzodioxole).

In each aspect of the invention it is often preferable that any alkyl, alkynyl or alkenyl moiety, including the hydrocarbon moiety of any alkoxy group, have less than 6 carbon atoms, preferably about 1 to 3 carbon atoms, and any cycloalkyl group have from about 3 to 7 carbon atoms.

The compounds of the invention may be prepared by the use of steps generally described in the literature or in the following Examples or by methods analogous or similar thereto and within the skill of the art.

For example, the compounds of the invention may be prepared using a 6-optionally substituted-2-(appropriately substituted heterocyclyl) heterobenzoic acid intermediate of the formula

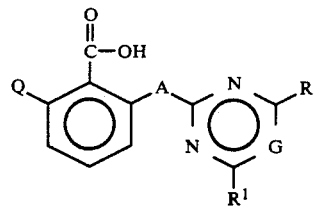

in which Q, A, G, R, and R$^1$ are the same as heretoabove described in Formula I.

The benzoic acid intermediate may be prepared by methods known in the arts. For example, the benzoic acid having an oxygen bridge was prepared by reacting an optionally substituted ortho-fluorobenzaldehyde with potassium hydroxide to form the corresponding optionally substituted salicylaldehyde. The optional substituent is preferably in, but not limited to, the 6-position. Thus, the product of the foregoing reaction would be a 6-optionally substituted salicylaldehyde. The 6-optionally substituted salicylaldehyde was in turn reacted with an inorganic base, e.g. potassium carbonate or sodium hydride, and an appropriately substituted heterocycle having a leaving group, such as chloro or methylsulfonyl, at the 2-position of the heterocyclic ring (e.g. 4,6-dimethoxy-2-methylsulfonylpyrimidine or 2-chloro-4,6-dimethoxy-1,3,5-triazine) to yield the corresponding benzaldehyde (e.g. 6-optionally substituted 2-(4,6-dimethoxypyrimidin-2-yloxy)benzaldehyde or 2-(4,6-dimethoxy-1,3,5-triazin-2-yloxy)benzaldehyde, respectively). The benzaldehyde was then oxidized to afford the corresponding benzoic acid intermediate of Formula III. Example 1, Steps D-F below illustrates this process.

The benzoic acid intermediate of Formula III having an oxygen or nitrogen bridge was prepared by reacting a benzyl 6-substituted salicylate or anthranilate, respectively, with sodium hydride and the appropriately substituted heterocycle, e.g. 4,6-dimethoxy-2-methylsulfonylpyrimidine, to yield the corresponding benzoate, e.g. benzyl 6-substituted 2-(4,6-dimethoxypyrimidin-2-yloxy)benzoate or 2-(4,6-dimethoxypyrimidin-2-ylamino)benzoate, respectively. The benzoate was subjected to hydrogenolysis in the presence of palladium on carbon to yield the corresponding benzoic acid, e.g. 6-substituted 2-(4,6-dimethoxypyrimidin-2-yloxy) benzoic acid or 2-(4,6-dimethoxypyrimidin-2-ylamino)benzoic acid, respectively. Example 2, Steps A-B and Example 3, Steps F-G, show this process.

The benzoic acid intermediate of Formula III having a sulfur bridge was prepared by reacting 6-optionally substituted anthranilic acid hydrochloride with fluoboric acid and sodium nitrite to yield the corresponding diazonium salt, 2-carboxy-3-optionally substituted benzenediazonium tetrafluoborate. The diazonium salt was in turn reacted with ethylxanthic acid potassium salt to afford the corresponding 6-optionally substituted-2-(ethoxythiocarbonylthio)benzoic acid. The benzoic acid was then hydrolyzed to yield the 6-optionally substituted-2-mercaptobenzoic acid. The mercaptobenzoic acid was reacted with sodium hydride and an appropriately substituted heterocycle, e.g. 4,6-dimethoxy-2-methysulfonylpyrimidine, to yield the corresponding benzoic acid of Formula III, e.g. 6-optionally substituted-2-(4,6-dimethoxypyrimidin-2-ylthio)benzoic acid. Example 5, Steps A-C, illustrates this process.

In an alternative route, the benzoic acid intermediate of Formula III in which Q is an optionally substituted alkyl or phenyl was also prepared using a process involving a 2-ethoxycarbonyl-3-(optionally substituted phenyl or alkyl)cyclohexen-5-one ester intermediate (intermediate IIa below) as described in F. M. Hauser et al., *Synthesis*, 10, 814 (1980). The following schema describes the synthetic route to intermediate IIa:

Step I

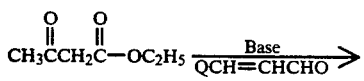

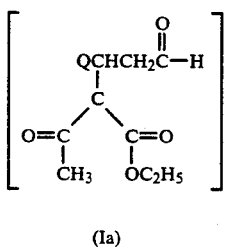

(Ia)

Step II

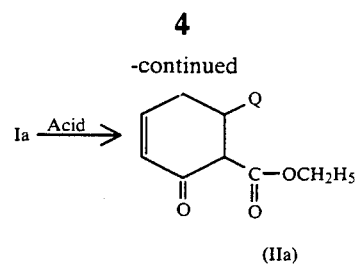

(IIa)

Intermediate IIa was prepared by reacting ethyl acetoacetate with the appropriately 3-(optionally substituted alkyl or phenyl)propenal in the presence of a base, such as sodium alkoxide (e.g. sodium ethoxide), to form the corresponding keto-aldehyde intermediate Ia which, without isolation, was thereafter cyclized by acid catalysis to the corresponding cyclohexenone intermediate IIa. See, for example, Example 6, Step A.

In the case of products having an oxygen bridge, the cyclohexenone intermediate IIa was then oxidized to the corresponding ethyl salicylate, e.g. ethyl 6-(optionally substituted phenyl or alkyl)salicylate, which was in turn hydrolyzed by basic catalysis to the corresponding salicylic acid, e.g. 6-(optionally substituted phenyl or alkyl)salicylic acid. The salicyclic acid was then reacted with sodium hydride and the appropriately substituted heterocycle, e.g. 4,6-dimethoxy-2-methylsulfonylpyrimidine, to yield the corresponding benzoic acid of Formula III, e.g. 6-(optionally substituted phenyl or alkyl)-2-(4,6-dimethoxypyrimidin-2-yloxy)benzoic acid. Example 6, Steps B-F illustrates this process.

To prepare products having a sulfur or amino bridge, the cyclohexenone intermediate IIa is reacted with phosphorous pentasulfide or ammonia, respectively, to yield the corresponding thioketo or imino ester, e.g. 2-ethoxycarbonyl-3-(optionally substituted phenyl or alkyl)cyclohex-5-enthione or 2-ethoxycarbonyl-3-(optionally substituted phenyl or alkyl)cyclohexenimine, respectively. The thioketo or imino ester is in turn reacted with an oxidant such as 2,3-dichloro-5,6-dicyano-1,4-benzoquinone and the like, to yield the corresponding benzoate or anthranilate, e.g. ethyl 2-mercapto-6-phenylbenzoate or ethyl 6-phenylanthranilate, respectively. The benzoate or anthranilate is subsequently reacted with potassium hydroxide in the presence of 1,4,7,10,13,16-hexaoxacyclooctadecane to yield the corresponding benzoic acid of Formula III, e.g. 2-mercapto-6-(substituted phenyl or alkyl)benzoic acid or 6-(substituted phenyl or alkyl)anthranilic acid, respectively.

The invention compounds of Formula I are afforded by reacting the benzoic acid intermediate of Formula III in one of two methods. When substituted at the 6-position, the appropriately substituted benzoic acid was reacted with dicyclohexylcarbodiimide and 4-nitrophenol to yield the corresponding 4-nitrophenyl benzoate. Reaction of the 4-nitrophenyl benzoate with potassium carbonate and an appropriately substituted sulfonamide yielded the targeted benzoylsulfonylamino heterocyclic compound of Formula I. Example 1 below, Steps G-I illustrates this method.

When unsubstituted at the 6-position, the benzoic acid intermediate was reacted directly with 1,1'-carbonyldiimidazole and the appropriately substituted sulfonamide to yield the targeted heterocyclic benzoylsulfonylamino compound of Formula I. This method is described in Example 2, Step C below.

EXAMPLE 1

SYNTHESIS OF 2-[3-CHLORO-2-(1-METHYLETHYLSULFONYLAMINOCARBONYL)PHENOXY]-4,6-DIMETHOXYPYRIMIDINE

Compound 10

Step A Synthesis of 4,6-dichloro-2-methylthiopyrimidine as an intermediate

Under a nitrogen atmosphere a stirred solution of 76.9 grams (0.49 mole) of 4,6-dihydroxy-2-methylthiopyrimidine and 190 mL (2.04 moles) of phosphorus oxychloride was heated at 95°–100° C. for two hours. After this time the reaction mixture was cooled to 5° C., and 250 mL of water was added dropwise during a 75 minute period. The mixture was warmed to 10° C., and an additional 500 mL of water was added during a 15 minute period. The resultant solid was collected by filtration and was washed with two 100 mL portions of water. The solid was dried to yield 84.7 grams of 4,6-dichloro-2-methylthiopyrimidine; m.p. 40.5°–42.5° C. The reaction was repeated several times.

Step B Synthesis of 4,6-dimethoxy-2-methylthiopyrimidine as an intermediate A stirred solution of 162.8 grams (0.832 mole) of 4,6-dichloro-2-methylthiopyrimidine in 325 mL of methanol was cooled to 15° C., and 419 mL (1.83 mole) of sodium methoxide (25% in methanol) was added dropwise at a rate to maintain the reaction mixture temperature below 20° C. Upon completion of the addition, which required 45 minutes, the reaction mixture was allowed to warm to ambient temperature where it was stirred for 18 hours. After this time the reaction mixture was concentrated under reduced pressure to a residual solid. The solid was dissolved in 850 mL of ethyl acetate. The solution was washed with one 500 mL portion and two 200 mL portions of water, and then with one 200 mL portion of an aqueous solution saturated with sodium chloride. The aqueous washes were combined and extracted with one 350 mL portion of ethyl acetate. The ethyl acetate extract was then washed with one 150 mL portion of an aqueous solution saturated with sodium chloride. The ethyl acetate layers and extracts were combined and dried with magnesium sulfate. The mixture was filtered, and the filtrate was concentrated under reduced pressure to yield 155.0 grams of 4,6-dimethoxy-2-methylthiopyrimidine, which solidified upon standing; m.p. 50°–52° C. The reaction was repeated several times.

Step C Synthesis of 4,6-dimethoxy-2-methylsulfonylpyrimidine as an intermediate A stirred solution of 143.6 grams (0.772 mole) of 4,6-dimethoxy-2-methylthiopyrimidine in 460 mL of tetrahydrofuran was cooled to 10°–15° C., and a cloudy solution of 525.0 grams (0.849 mole) of 80% monoperoxyphthalic acid, magnesium salt hexahydrate in 600 mL of methanol was added at a rate to maintain the reaction mixture temperature below 15° C. Upon completion of the addition, which required one hour, the reaction mixture was cooled, and 500 mL of aqueous 1M sodium sulfite solution was added dropwise to destroy excess peroxides present in the reaction mixture. Upon completion of addition, the reaction mixture was stirred for 15 minutes and then was concentrated under reduced pressure to a residue. The residue was stirred in 2500 mL of ethyl acetate and 1500 mL of water. The layers were separated, and the aqueous layer was extracted with 450 mL of ethyl acetate. The ethyl acetate layers were combined and washed with one 500 mL portion of water, two 350 mL portions of aqueous 20% potassium carbonate, two 350 mL portions of water, and one 300 mL portion of an aqueous solution saturated with sodium chloride. The organic layer was dried with magnesium sulfate and filtered. The filtrate was concentrated under reduced pressure to yield 123.3 grams of 4,6-dimethoxy-2-methylsulfonylpyrimidine; m.p. 126°–127.5° C. The reaction was repeated several times.

Step D Synthesis of 6-chlorosalicylaldehyde as an intermediate

A stirred solution of 40.0 grams (0.252 mole) of 2-chloro-6-fluorobenzaladehyde in 300 mL of dimethylsulfoxide was cooled to 15° C., and 36.6 grams (0.555 mole) of powdered 85% potassium hydroxide was added portionwise at a rate to maintain the reaction mixture temperature below 25° C. Upon completion of addition, the reaction mixture was stirred at ambient temperature for 18 hours. After this time the reaction mixture was poured into 1000 mL of water and was acidified with concentrated hydrochloric acid, with stirring. The resultant solid was collected by filtration, washed with water, and dried to yield 30.1 grams of 6-chlorosalicylaldehyde; m.p. 50°–52° C.

Step E Synthesis of 6-chloro-2-(4,6-dimethoxypyrimidin-2-yloxy)benzaldehyde as an intermediate Under a nitrogen atmosphere a solution of 2.0 grams (0.013 mole) of 6-chlorosalicylaldehyde in 10 mL of dimethylformamide was stirred, and 1.94 grams (0.0141 mole) of potassium carbonate was added. The reaction mixture was then stirred for 10 minutes, and a solution of 2.6 grams (0.013 mole) of 4,6-dimethoxy-2-methylsulfonylpyrimidine (prepared in Steps A–C) in 15 mL of dimethylformamide was added dropwise during a 10 minute period. Upon completion of addition, the reaction mixture was warmed to 60° C. where it was stirred for 18 hours. The reaction mixture was poured into 150 mL of water, cooled, and the pH was adjusted to 12 with aqueous 50% sodium hydroxide, with stirring. The mixture was stirred for 15 minutes, and the resultant solid was collected by filtration to yield 1.62 grams of 6-chloro-2-(4,6-dimethoxypyrimidin-2-yloxy)benzaldehyde. The nmr spectrum was consistent with the proposed structure. The reaction was repeated several times.

Step F Synthesis of 6-chloro-2-(4,6-dimethoxypyrimidin-2-yloxy)benzoic acid as an intermediate To stirred solution of 9.6 grams (0.033 mole) of 6-chloro-2-(4,6-dimethoxypyrimidin-2-yloxy)benzaldehyde in 260 mL of acetone was added dropwise a solution of 7.7 grams (0.049 mole) of potassium permanganate and 6.6 grams (0.024 mole) of sodium phosphate dibasic heptahydrate in 105 mL of water while maintaining the reaction mixture temperature at 20°–25° C. Upon completion of addition, the reaction mixture was stirred at ambient temperature for 18 hours. After this time sodium thiosulfate was added to the reaction mixture to destroy excess permanganate. The reaction mixture was then filtered through diatomaceous earth. The filtrate was cooled and acidified to a pH of 3-4 with aqueous 10% hydrochloric acid. The mixture was extracted with two 50 mL portions of methylene chloride. The combined extracts were dried with magnesium sulfate and filtered. The filtrate was concentrated under reduced pressure to a residue. The residue was crystallized from methylene chloride and carbon tetrachloride to yield 10.0 grams of 6-chloro-2-(4,6-dimethoxypyrimidin-2-yloxy)benzoic acid. The nmr spectrum was consistent with the proposed structure.

Step G Synthesis of 4-nitrophenyl 6-chloro-2-(4,6-dimethoxypyrimidin-2-yloxy)benzoate as an intermediate To a stirred solution of 5.4 grams (0.017 mole) of 6-chloro-2-(4,6-dimethoxypyrimidin-2-yloxy)benzoic acid in 25 mL of methylene chloride was added 2.4 grams (0.017 mole) of 4-nitrophenol. The reaction mixture was cooled to 0° C., and 3.5 grams (0.017 mole) of dicyclohexylcarbodiimide was added. Upon completion of addition, the reaction mixture was stirred at 0° C. for 30 minutes, and then it was warmed to ambient temperature where it was stirred for an additional two hours. The reaction mixture was filtered, and the filtrate was concentrated under reduced pressure to a residue. The residue was stirred with diethyl ether, and the resultant solid was collected by filtration to yield 5.4 grams of 4-nitrophenyl 6-chloro-2-(4,6-dimethoxypyrimidin-2-yloxy)benzoate, m.p. 130°-132° C. The nmr spectrum was consistent with the proposed structure.

Step H Synthesis of 1-methylethylsulfonamide as an intermediate

Ammonia gas, 4.5 mL (excess), was condensed into the reaction vessel and cooled to −40° C. With stirring, 3.0 grams (0.021 mole) of 1-methylethylsulfonyl chloride in 15 mL of cold diethyl ether was added dropwise. Upon completion of addition, the reaction mixture was allowed to warm to 0° C. during a one hour period and then to ambient temperature where it stirred for 18 hours. The reaction mixture was filtered, and the filtrate was concentrated under reduced pressure to yield 2.0 grams of 1-methylethylsulfonamide; m.p. 51°-57° C. The nmr spectrum was consistent with the proposed structure.

Step I Synthesis of 2-[3-chloro-2-(1-methylethylsulfonylaminocarbonyl)-phenoxy]-4,6-dimethoxypyrimidine (Compound 10)

A stirred solution of 0.43 grams (0.001 mole) of 4-nitrophenyl 6-chloro-2-(4,6-dimethoxypyrimidin-2-yloxy)benzoate (prepared in Steps F and G), 0.12 gram (0.001 mole) of 1-methylethylsulfonamide, and 0.14 gram (0.001 mole) of potassium carbonate in 5 mL of acetonitrile was heated at reflux for five hours. The reaction mixture was then cooled and concentrated under reduced pressure to a residue. The residue was stirred with ethyl acetate and water, and the aqueous layer was separated. The aqueous layer was acidified with aqueous dilute hydrochloric acid and then was extracted with ethyl acetate. The extract was dried with magnesium sulfate and filtered. The filtrate was concentrated under reduced pressure to a residue. The residue was crystallized from diethyl ether. The solid was collected by filtration to yield 0.16 gram of 2-[3-chloro-2-(1-methylethylsulfonylaminocarbonyl)phenoxy]-4,6dimethoxypyrimidine; m.p. 150°-152° C., Compound 10 in Table 1. The nmr spectrum was consistent with the proposed structure.

EXAMPLE 2

SYNTHESIS OF 2-[2-(1-METHYLETHYLSULFONYLAMINOCARBONYL)PHENOXY]-4,6-DIMETHOXYPYRIMIDINE

Compound 9

Step A Synthesis of ethyl 2-(4,6-dimethoxypyrimidin-2-yloxy)benzoate as an intermediate After washing with petroleum ether, 3.9 grams (0.079 mole) of 60% sodium hydride in mineral oil was suspended in 15 mL of dimethylformamide. The suspension was cooled, and a solution of 10.8 grams (0.065 mole) of ethyl salicylate in 20 mL of dimethylformamide was added dropwise with stirring. Upon completion of addition, the reaction mixture was stirred at ambient temperature for one hour, and then 10.5 grams (0.048 mole) of 4,6-dimethoxy-2-methylsulfonylpyrimidine (prepared as in Example 1, Steps A–C) was added. Upon completion of addition, the reaction mixture was heated at 100° C. for 2.5 hours. The reaction mixture was cooled and poured into 250 mL of water. The mixture was extracted with ethyl acetate, and the extract was dried with magnesium sulfate. The mixture was filtered, and the filtrate was subjected to column chromatography on silica gel. Elution was accomplished using in succession 25% hexane in methylene chloride and 30% ethyl acetate in hexane. The appropriate fractions were combined and concentrated under reduced pressure to yield 12.5 grams of ethyl 2-(4,6-dimethoxypyrimidin-2-yloxy)benzoate. The nmr spectrum was consistent with the proposed structure.

Step B Synthesis of 2-(4,6-dimethoxypyrimidin-2-yloxy)benzoic acid as an intermediate To a stirred solution of 7.5 grams (0.025 mole) of ethyl 2-(4,6-dimethoxypyrimidin-2-yloxy)tenzoate in 13 mL of ethanol was added a solution of 3.5 grams (0.061 mole) of 85% potassium hydroxide in 13 mL of water. Upon completion of addition, the reaction mixture was stirred for two hours. The reaction mixture was then poured into water, and this mixture was acidified to a pH of 1 with concentrated hydrochloric acid. The mixture was extracted with ethyl acetate, and the extracts were dried with magnesium sulfate. The mixture was filtered, and the filtrate was concentrated under reduced pressure to a residue. The residue was slurried in diethyl ether/petroleum ether and collected by filtration to yield 4.5 grams of 2-(4,6-dimethoxypyrimidin-2-yloxy)benzoic acid. The nmr spectrum was consistent with the proposed structure.

Step C Synthesis of 2-[2-(1-methylethylsulfonylaminocarbonyl)phenoxy]-4,6-dimethoxypyrimidine (Compound 9)

To a stirred suspension of 0.33 gram (0.002 mole) of 1,1'-carbonyldiimidazole in 2 mL of tetrahydrofuran was added dropwise a solution of 0.55 gram (0.002 mole) of 2-(4,6-dimethoxypyrimidin-2-yloxy)benzoic acid in 3 mL of tetrahydrofuran. Upon completion of addition, the reaction mixture was stirred at ambient temperature for 30 minutes, and then it was heated to reflux where it was stirred for an additional 30 minutes. After this time the reaction mixture was cooled, and 0.25 gram (0.002 mole) of 1-methylethylsulfonamide (prepared as in Example 1—Step H) was added. Upon completion of addition, the reaction mixture was stirred for 10 minutes, and 0.31 gram (0.002 mole) of 1,8-diazabicyclo[5.4.0]undec-7-ene was added. Upon completion of addition, the reaction mixture was stirred at ambient temperature for five hours. The reaction mixture was then poured into aqueous dilute hydrochloric acid. The mixture was extracted with ethyl acetate, and the extract was dried with magnesium sulfate. The mixture was filtered, and the filtrate was concentrated under reduced pressure to a residue. The residue was subjected to column chromatography on silica gel. Elution was accomplished using 10% and 20% ethyl acetate in methylene chloride. The appropriate fractions were combined and concentrated under reduced pressure to yield 0.2 gram of 2-[2-(1-methylethylsulfonylaminocarbonyl)phenoxy]-4,6-dimethoxypyrimidine; m.p. 128°-130° C., Compound 9 in Table I. The nmr spectrum was consistent with the proposed structure.

EXAMPLE 3

SYNTHESIS OF
2-[3-CHLORO-2-(METHYLSULFONYLAMINOCARBONYL)PHENOXY]-4,6-DIMETHOXY-1,3,5-TRIAZINE

Compound 38

Step A Synthesis of
6-chloro-2-(methylcarbonylamino)benzoic acid as an intermediate A stirred solution of 85.2 grams (0.47 mole) of 2-methyl-3 chloroacetanilide in 4000 mL of water was warmed to 80°-85° C., and 513.0 grams (1.45 moles) of aqueous 40% sodium permanganate was added portionwise during a 3.5 hour period. Upon completion of addition, the reaction was stirred at 80°-85° C. for about 18 hours. After this time the reaction mixture was cooled to ambient temperature and was filtered through diatomaceous earth. The filter cake was washed with water, and the wash and filtrate were combined. The combination was cooled to 10° C. and, with vigorous stirring, was acidified to pH 2 with concentrated hydrochloric acid. The resultant solid was collected by filtration and was tritrated with acetone. The solid was dried to yield 6-chloro-2-(methylcarbonylamino)benzoic acid. The nmr spectrum was consistent with the proposed structure.

Step B Synthesis of 6-chloroanthranilic acid hydrochloride as an intermediate

A mixture of 20.0 grams (0.093 mole) of 6-chloro-2-(methylcarbonylamino)benzoic acid in 150 mL of concentrated hydrochloric acid was stirred at 80° for about 3 hours. The reaction mixture was cooled to ambient temperature and was filtered to collect a solid. The solid was washed with cold diethyl ether and dried to yield 20.3 grams of 6-chloroanthranilic acid hydrochloride; m.p. 194°-195° C. The nmr spectrum was consistent with the proposed structure.

Step C Synthesis of 6-chlorosalicylic acid as an intermediate

A stirred suspension of 10.0 grams (0.048 mole) of 6-chloroanthranilic acid hydrochloride and 100 mL of concentrated hydrochloric acid in 200 mL of water was cooled to 5° C., and a solution of 3.5 grams (0.050 mole) of sodium nitrite in 50 mL of water was added dropwise during a 10 minute period. Upon completion of addition, the reaction mixture was warmed to 90° C. where it was stirred for about 10 minutes. The reaction mixture was cooled to ambient temperature and was filtered. The filter cake was washed with cold heptane and dried to yield 3.7 grams of 6-chlorosalicylic acid. The nmr spectrum was consistent with the proposed structure.

Step D Synthesis of phenylmethyl 6-chlorosalicylate as an intermediate

Under a nitrogen atmosphere, a solution of 5.7 grams (0.033 mole) of 6-chlorosalicylic acid in 200 mL of dimethylformamide was vigorously stirred, and 1.3 grams (0.033 mole) of 60% sodium hydride in mineral oil was added in one portion. Upon completion of addition, the reaction mixture was stirred for approximately 5 minutes until evolution of hydrogen gas had ceased. After this time 4.2 grams (0.033 mole) of benzyl chloride and 5.0 grams (0.033 mole) of sodium iodide were each added in one portion. Upon completion of addition, the reaction mixture was stirred at ambient temperature for about 30 hours. After this time the reaction mixture was poured into a mixture of 150 mL of aqueous 3N hydrochloric acid and 300 mL of an aqueous solution saturated with sodium chloride. The mixture was extracted with three 250 mL portions of diethyl ether. The ether extracts were combined, and the combination was washed with two 250 mL portions of an aqueous solution saturated with sodium chloride. The aqueous washes were combined and extracted with one 250 mL portion of ethyl acetate. The ethyl acetate extract was then washed with three 100 mL portions of an aqueous solution saturated with sodium chloride. The diethyl ether and ethyl acetate extracts were combined and were dried with magnesium sulfate. The mixture was filtered, and the filtrate was concentrated under reduced pressure to a residue. The residue was adsorbed onto silica gel and was subjected to column chromatography. Elution was accomplished with 10% ethyl acetate in heptane. The appropriate fractions were combined and concentrated under reduced pressure to yield 5.5 grams of phenylmethyl 6-chlorosalicylate. The nmr spectrum was consistent with the proposed structure.

Step E Synthesis of
2-chloro-4,6-dimethoxy-1,3,5-triazine as an intermediate

To a stirred mixture of 45.0 grams of methanol and 5.0 grams of water was added 16.8 grams (0.2 mole) of sodium bicarbonate and 18.5 grams (0.1 mole) of cyanuric chloride. The addition caused the reaction mixture temperature to rise to 35° C. and the liberation of carbon dioxide gas. After the gas evolution slowed, the reaction mixture was heated to reflux where it stirred for 30 minutes. The reaction mixture was cooled, diluted with water, and the resultant solid was collected by filtration. The solid was washed repeatedly with water and dried to yield 13.0 grams of 2-chloro-4,6-dimethoxy-1,3,5-triazine, m.p. 74°-76° C. Recrystallization of the solid from heptane raised the melting point to 75°-76° C.

Step F Synthesis of phenylmethyl 6-chloro 2-(4,6-dimethoxy-1,3,5-triazin-2-yloxy)benzoate as an intermediate A solution of 2.0 grams (0.008 mole) of phenylmethyl 6-chlorosalicylate (prepared in Steps A-D) in 25 grams of dimethylformamide was stirred, and 0.3 gram (0.008 mole) of 60% sodium hydride in mineral oil was added. The addition caused the reaction mixture temperature to rise to 32° C. The reaction mixture was allowed to cool to ambient temperature, at which 1.3 grams (0.008 mole) of 2-chloro-4,6-dimethoxy-1,3,5-triazine was added in one portion. Upon completion of addition, the reaction mixture was stirred at ambient temperature for 4 hours. After this time an aliquot of the reaction mixture was subjected to thin layer chromatography, which indicated the reaction mixture had not gone to completion. The reaction mixture was warmed to 80°-85° C. where it was stirred for about 18 hours. After this time the reaction mixture was cooled to ambient temperature and then was poured into a mixture of 100 mL of aqueous 3N hydrochloric acid and 100 mL of an aqueous solution saturated with sodium chloride. The mixture was o extracted with two 300 mL portions of diethyl ether. The combined extracts were washed with one 250 mL portion of an aqueous solution saturated with sodium chloride. The organic layer was dried with magnesium sulfate and filtered. The filtrate was concentrated under reduced pressure to a point where a solid residue appeared. The residue was slurried in 5 mL of diethyl ether and filtered to yield 0.6 gram of phenylmethyl 6-chloro-2-(4,6-dimethoxy-1,3,5-triazin-2-yloxy)benzoate. The nmr spectrum was consistent with the proposed structure.

Step G Synthesis of 6-chloro-2-(4,6-dimethoxy-1,3,5-triazin-2 yloxy)benzoic acid as an intermediate A solution of 0.6 gram (0.001 mole) of phenylmethyl 6-chloro-2-(4,6-dimethoxy-1,3,5-triazin-2-yloxy)benzoate in 50 mL of ethanol and 15 mL of acetic acid was hydrogenated in the presence of 5% palladium on charcoal using a Parr hydrogenation apparatus. Upon completion of the hydrogenation, the reaction mixture was filtered through diatomaceous earth. The diatomaceous earth filter cake was washed with tetrahydrofuran. The combined filtrate and wash was concentrated under reduced pressure to a residue. The residue was dissolved in 150 mL of methylene chloride and was washed with two 150 mL portions of an aqueous solution saturated with sodium chloride. The organic layer was dried with magnesium sulfate and filtered. The filtrate was concentrated under reduced pressure to a residue. The residue was stirred in 10 mL of diethyl ether containing a few drops of heptane. The resultant solid was collected by filtration and was washed with cold diethyl ether to yield 0.26 gram of 2-chloro-6-(4,6-dimethoxy-1,3,5-triazin-2-yloxy)benzoic acid. The nmr spectrum was consistent with the proposed structure.

Step H Synthesis of 4-nitrophenyl 6-chloro-2-(4,6-dimethoxy-1,3,5-triazin-2-yloxy)benzoate as an intermediate This compound is prepared in a manner analogous to that of Example 1, Step G, using equimolar amounts of 6-chloro-2-(4,6-dimethoxy-1,3,5-triazin-2-yloxy)benzoic acid, 4-nitrophenol, and dicyclohexylcarbodiimide in methylene chloride to yield 4-nitrophenyl 6-chloro-2-(4,6-dimethoxy-1,3,5-triazin-2-yloxy)benzoate.

Step I Synthesis of 2-[3-chloro-2-(methylsulfonylaminocarbonyl)phenoxy]-4,6-dimethoxy-1,3,5-triazine This compound is prepared in a manner analogous to that of Example 1, Step I, using equimolar amounts of 4-nitrophenyl 2-chloro-6-(4,6-dimethoxy-1,3,5-triazin-2-yloxy)benzoate, methanesulfonamide, and potassium carbonate in acetonitrile to yield 2-[3-chloro-2-(methylsulfonylaminocarbonyl)phenoxy]-4,6-dimethoxy-1,3,5-triazine, Compound 38 of Table 1.

EXAMPLE 4

SYNTHESIS OF 2-[3-CHLORO-2-(METHYLSULFONYLAMINOCARBONYL)PHENYLAMINO]-4,6-DIMETHOXYPYRIMIDINE

Compound 39

Step A Synthesis of phenylmethyl 6-chloroanthranilate as an intermediate

Under a nitrogen atmosphere a solution of 6.4 grams (0.031 mole) of 6-chloroanthranilic acid hydrochloride (prepared as in Example 3, Step B), 3.9 grams (0.031 mole) of benzyl chloride, and 6.2 grams (0.062 mole) of potassium bicarbonate in 100 mL of dimethylformamide was stirred at ambient temperature for about 48 hours. After this time the reaction mixture was poured into 250 mL of an aqueous solution saturated with sodium chloride. The mixture was extracted with three 250 mL portions of diethyl ether. The combined extracts were washed with one 250 mL portion of an aqueous solution saturated with sodium chloride. The organic layer was dried with magnesium sulfate and filtered. The filtrate was concentrated under reduced pressure to a residue. The residue was subjected to column chromatography on silica gel. Elution was accomplished using 20% ethyl acetate in heptane. The appropriate fractions were combined and concentrated under reduced pressure to yield 6.4 grams of phenylmethyl 6-chloroanthranilate. The nmr spectrum was consistent with the proposed structure.

Step B Synthesis of phenylmethyl 6-chloro-2-(4,6-dimethoxypyrimidin-2-ylamino)benzoate as an intermediate Under a nitrogen atmosphere a solution of 5.2 grams (0.020 mole) of phenylmethyl 6-chloroanthranilate in 150 mL of tetrahydrofuran was stirred, and 0.8 gram (0.02 mole) of 60% sodium hydride in mineral was added in one portion. Upon completion of addition, the reaction mixture was stirred for 5 minutes, and the reaction mixture temperature was slowly brought to 50° C. After this time 4.3 grams (0.020 mole) of 4,6-dimethoxy-2-methylsulfonylpyrimidine (prepared as in Example 1, Steps A-C) was added in one portion. Upon completion of - addition, the reaction mixture was warmed to reflux where it was stirred for about 18 hours. The reaction mixture was cooled to ambient temperature and was poured into a solution of 50 mL of 3N hydrochloric acid and 200 mL of an aqueous solution saturated with sodium chloride. The mixture was extracted with three 250 mL portions of diethyl ether. The combined extracts were washed with one 250 mL portion of an aqueous solution saturated with sodium chloride. The organic layer was dried with magnesium sulfate and filtered. The filtrate was concentrated under reduced pressure to a residual oil. The oil was adsorbed onto silica gel and was subjected to column chromatography on silica gel. Elution was accomplished with 20% ethyl acetate in hexane. The appropriate fractions were combined and concentrated under reduced pressure to yield 4.0 grams of phenylmethyl 6-chloro-2-(4,6-dimethoxypyrimidin-2-ylamino)benzoate. The nmr spectrum was consistent with the proposed structure.

Step C Synthesis of 6-chloro-2-(4,6-dimethoxypyrimidin-2-ylamino)benzoic acid as an intermediate This compound was prepared in a manner analogous to that of Example 3, Step G, using 2.0 grams (.005 mole) of phenylmethyl 6-chloro-2-(4,6-dimethoxypyrimidin-2-ylamino)benzoate, 0.2 g (catalyst) of 5% palladium on charcoal, hydrogen gas, 35 mL of acetic acid, and 50 mL of ethanol. The yield of 6-chloro-2-(4,6-dimethoxypyrimidin-2-ylamino)benzoic acid Was 0.3 gram. The nmr spectrum was consistent With the proposed structure.

Step D Synthesis of 4-nitrophenyl 6-chloro-2-(4,6-dimethoxypyrimidin-2-ylamino)benzoate This compound is prepared in a manner analogous to that of Example 1, Step G, using equimolar amounts of 6-chloro-2-(4,6-dimethoxypyrimidin-2-ylamino)benzoic acid, 4-nitrophenol, and dicyclohexylcarbodiimide in methylene chloride to yield 4-nitrophenyl 6-chloro-2-(4,6-dimethoxypyrimidin-2-ylamino)benzoate.

Step E Synthesis of 2-[3-chloro-2-(methylsulfonylaminocarbonyl)-phenylamino]-4,6-dimethoxypyrimidine This compound is prepared in a manner analogous to that of Example 1, Step I, using equimolar amounts of 4-nitrophenyl 6-chloro-2-(4,6-dimethoxypyrimidin-2-ylamino)benzoate, methanesulfonamide, and potassium carbonate in acetonitrile, yielding 2-[3-chloro-2-(methylsulfonylaminocarbonyl)phenylamino]-4,6-dimethoxypyrimidine, Compound 39 of Table 1.

EXAMPLE 5

SYNTHESIS OF 2-[3-CHLORO-2-(METHYLSULFONYLAMINOCARBONYL)PHENYLTHIO]-4,6-DIMETHOXYPYRIMIDINE

Compound 40

Step A Synthesis of 2-carboxy-3-chlorobenzenediazonium tetrafluoborate as an intermediate A stirred suspension of 5.0 grams (0.024 mole) of 6-chloroanthranilic acid hydrochloride (prepared as in Example 3, Step B) in 20 mL of fluoboric acid was cooled to 0° C., and a solution of 1.8 grams (0.029 mole) of sodium nitrite in 10 mL of water was added dropwise during a 5 minute period. Upon completion of addition, the reaction mixture was allowed to warm to 15° C. where it was stirred for 30 minutes. After this time the reaction mixture was placed in a freezer where it was stored for about 48 hours. The reaction mixture was filtered to collect a solid. The solid was washed with dry ice acetone, cold 1:1—diethyl ether—methanol, and cold diethyl ether to yield 2.0 grams of 2-carboxy-3-chlorobenzenediazonium tetrafluoborate, m.p. 120°–125° C.

Step B Synthesis of 6-chloro-2-[ethoxy(thiocarbonyl)-thio]benzoic acid as an intermediate To a stirred suspension of 2.4 grams (0.014 mole) of ethylxanthic acid, potassium salt in 30 mL of acetone was added, by pipette, a stirred suspension of 2.0 grams (0.007 mole) of 2-carboxy-3-chlorobenzenediazonium tetrafluoborate in 50 mL of acetone. The flask containing the fluoborate suspension was rinsed with 20 mL of acetone, and the rinse was added to the reaction mixture. Upon completion of addition which required 7 minutes, the reaction mixture was stirred for about 18 hours. The reaction mixture was filtered to collect 2.0 grams of 6-chloro-2-[ethoxy(thiocarbonyl)thio]benzoic acid. The nmr spectrum was consistent with the proposed structure.

Step C Synthesis of 6-chloro-2-mercaptobenzoic acid as an intermediate

To a stirred solution of 2.0 grams (0.007 mole) of 6-chloro-2-[ethoxy(thiocarbonyl)thio]benzoic acid in 50 mL of methanol was added 30 ml of aqueous 10% sodium hydroxide. The reaction mixture was warmed to reflux where it stirred for about 18 hours. After this time the reaction mixture was cooled to ambient temperature and was acidified with concentrated hydrochloric acid. The mixture was extracted with ethyl acetate, and the extract was dried with magnesium sulfate. The mixture was filtered, and the filtrate was concentrated under reduced pressure to yield 1.4 grams of 6-chloro-2-mercaptobenzoic acid. The nmr spectrum was consistent with the proposed structure.

Step D Synthesis of 6-chloro-2-(4,6-dimethoxypyrimidin-2-ylthio)benzoic acid as an intermediate A solution of 1.4 grams (0.007 mole) of 6-chloro-2-mercaptobenzoic acid in 50 mL of dimethylformamide was stirred, and 0.6 gram (0.01 mole) of 60% sodium hydride in mineral oil was added in two portions during a 3 minute period. After this time the reaction mixture was stirred for 30 minutes, and 1.6 grams (0.007 mole) of 4,6-dimethoxy-2-methylsulfonylpyrimidine (prepared as in Example 1, Steps A–C) was added. Upon completion of addition, the reaction mixture was stirred for about 60 hours. After this time the reaction mixture was poured into 150 mL of an aqueous solution saturated with sodium chloride. Water, 50 mL, was added, and the mixture was extracted with three 70 mL portions of ethyl acetate. The combined extracts were evaporated under reduced pressure, leaving no residue. The aqueous layer was cooled and acidified to pH 2 with aqueous 3N hydrochloric acid. The mixture was reextracted with three 70 mL portions of ethyl acetate. The combined extracts were washed with four 50 mL portions of an aqueous solution saturated with sodium chloride. The organic layer was concentrated under reduced pressure to a residue. The residue was subjected to two purifications by column chromatography on silica gel. Elution for the first purification was accomplished using 10% methanol in methylene chloride, and with 33% acetone in methylene chloride for the second purification. The yield of 6-chloro-2-(4,6-dimethoxypyrimidin-2-ylthio)benzoic acid was 0.3 gram. The nmr spectrum was consistent with the proposed structure.

Step E Synthesis of 4-nitrophenyl 6-chloro-2-(4,6-dimethoxypyrimidin-2-ylthio)benzoate as an intermediate This compound is prepared in a manner analogous to that of Example 1, Step G, using equimolar amounts of 6-chloro-2-(4,6-dimethoxypyrimidin-2-ylthio)benzoic acid, 4-nitrophenol, and dicyclohexylcarbodiimide in methylene chloride, yielding 4-nitrophenyl 6-chloro-2-(4,6-dimethoxypyrimidin-2-ylthio)benzoate.

Step F Synthesis of 2-[3-chloro-2-(methylsulfonylaminocarbonyl)phenylthio]-4,6-dimethoxypyrimidine This compound is prepared in a manner analogous to that of Example 1, Step I, using equimolar amounts of 4-nitrophenyl 6-chloro-2-(4,6-dimethoxypyrimidin-2-ylthio)benzoate, methanesulfonamide, and potassium carbonate in acetonitrile to yield 2-[3-chloro-2-(methylsulfonylaminocarbonyl)phenylthio]-4,6-dimethoxyprimidine, Compound 40 of Table 1.

EXAMPLE 6

SYNTHESIS OF 2-[3-PHENYL-2-(METHYLSULFONYLAMINOCARBONYL)PHENOXY]-4,6-DIMETHOXYPYRIMIDINE

Compound 41

Step A Synthesis of 2-ethoxycarbonyl-3-phenylcyclohex-5-enone as an intermediate Under a nitrogen atmosphere, 0.1 gram (0.004 mole) of sodium metal was reacted in 40 mL of ethanol. The solution was stirred, and 13.0 grams (0.100 mole) of ethyl acetoacetate was added. The reaction mixture was cooled in an ice bath, and 13.2 grams (0.100 mole) of trans-cinnamaldehyde in 10 mL of ethanol was added dropwise during a 10 minute period. Upon completion of addition, the reaction mixture was allowed to warm to ambient temperature where it stirred for about 18 hours. After this time the reaction mixture was saturated with gaseous hydrochloric acid and then was allowed to stand for about 65 hours. The reaction mixture was concentrated under reduced pressure to yield 2-ethoxycarbonyl-3-phenylcyclohex-5-enone. A 100% yield (24.4 grams) of product was assumed.

The reaction was repeated replacing the sodium metal with ethyl acetoacetate, sodium salt. Thus, 12.6 grams (0.097 mole) of ethyl acetoacetate, 0.5 gram (0.003 mole) of ethyl acetoacetate, sodium salt and 13.2 grams (0.100 mole) of trans-cinnamaldehyde in 50 mL of ethanol were reacted in a manner analogous to that of Example 6, Step A. A 100% yield (24.4 grams) of 2-ethoxycarbonyl-3-phenylcyclohex-5-enone was assumed.

Step B Synthesis of ethyl 6-phenylsalicylate as an intermediate

Under a nitrogen atmosphere, a stirred solution of 24.4 grams (0.100 mole) of crude 2-ethoxycarbonyl-3-phenylcyclohex-5-enone in 50 mL of carbon tetrachloride was cooled in an ice bath, and a solution of 16.1 grams (0.100 mole) of bromine in 50mL of acetic acid was added dropwise. Upon completion of addition, the reaction mixture was stirred at the ice-bath temperature for 30 minutes. After this time the reaction mixture was warmed to reflux where it was stirred for about 21 hours. The reaction mixture was cooled and then was stirred with 80 mL of methylene chloride and 80 mL of water. The layers were separated, and the organic layer was washed with two portions of water and with one portion of an aqueous solution saturated with sodium bicarbonate. The organic layer was dried with sodium sulfate and magnesium sulfate and then was filtered. The filtrate was concentrated under reduced pressure to a residue. The residue was subjected to column chromatography on silica gel. Elution was accomplished using 2:1-heptane and methylene chloride. The appropriate fractions were combined and concentrated under reduced pressure to yield 7.1 grams of ethyl 6-phenylsalicylate. The nmr spectrum was consistent with the proposed structure.

Step C Synthesis of 6-phenylsalicylic acid as an intermediate

To a stirred solution of 3.3 grams (0.014 mole) of ethyl 6-phenylsalicylate in 30 mL of ethanol was added a catalytic amount of 1,4,7,10,13,16-hexaoxacyclooctadecane. This was followed by the addition of a solution of 2.0 grams (0.030 mole) of 85% potassium hydroxide in 15 mL of water. Upon completion of addition, the reaction mixture was warmed to reflux where it was stirred for 4 hours. The reaction mixture was allowed to cool to ambient temperature where it stood for about 18 hours. After this time the reaction mixture was again warmed to reflux where it stirred for 4 hours. Thin layer chromatographic analysis of the reaction mixture indicated the reaction had not gone to completion. An additional 0.3 gram of 85% potassium hydroxide was added to the reaction mixture and the heating at reflux was continued for another 3 hours. After this time the reaction mixture was cooled, and volatile materials were removed under reduced pressure. The aqueous concentrate was washed with two portions of diethyl ether. The combined ether washes were backwashed with water. The water washes and the aqueous concentrate were combined, and the combination was acidified to pH 1 with concentrated hydrochloric acid. The mixture was extracted with three portions of ethyl acetate. The combined extracts were dried with magnesium sulfate and filtered. The filtrate was concentrated under reduced pressure to a residue. The residue was dissolved in hot ethanol, and the solution was treated with decolorizing carbon. The mixture was filtered through diatomaceous earth, and the filtrate was concentrated under reduced pressure to a residue. The residue was recrystallized from diethyl ether and hexane to yield 6-phenylsalicylic acid, m.p. 143°–146°. The filtrate from the recrystallization was concentrated under reduced pressure to a residual solid. The residue was combined with the 6-phenylsalicylic acid, m.p. 143°–146° C., yielding 2.8 grams of this material.

Step D Synthesis of 6-phenyl-2-(4,6-dimethoxypyrimidin-2-yloxy)benzoic acid as an intermediate This compound was prepared in a manner analogous to that of Example 5, Step D, using 0.5 gram (0.003 mole) of 6-phenylsalicylic acid, 0.6 gram (0.003 mole) of 4,6-dimethoxy-2-methylsulfonylpyrimidine, and 0.3 gram (0.005 mole) of 50% sodium hydride in mineral oil in 60 mL of tetrahydrofuran. This reaction mixture was combined with a second reaction mixture of 1.7 grams (0.008 mole) of 6-phenylsalicylic acid, 1.7 grams (.008 mole) of 4,6-dimethoxy-2-methylsulfonylpyrimidine and 0.8 gram (0.016 mole) of 50% sodium hydride in mineral oil in 120 mL of tetrahydrofuran. The combination was treated as described in Example 5, Step D, to yield 1.7 grams of 6-phenyl-2-(4,6-dimethoxypyrimidin-2-yloxy)benzoic acid. The nmr spectrum was consistent with the proposed structure.

Step E Synthesis of 4-nitrophenyl 6-phenyl-2-(4,6-dimethoxypyrimidin-2-yloxy)benzoate as an intermediate This compound is prepared in a manner analogous to that of Example 1, Step G, using equimolar amounts of 6-phenyl-2-(4,6-dimethoxypyrimidin-2-yloxy)benzoic acid, 4-nitrophenol, and dicyclohexylcarbiimide in methylene chloride, yielding 4-nitrophenyl 6-phenyl-2-(4,6-dimethoxypyrimidin-2-yloxy)benzoate.

Step F Synthesis of 2-[3-phenyl-2-(methylsulfonylaminocarbonyl)phenoxy]-4,6-dimethoxypyrimidine

Compound 41

This compound is prepared in a manner analogous to that of Example 1, Step I, using equimolar amounts of 4-nitrophenyl 6-phenyl-2-(4,6-dimethoxypyrimidin-2-yloxy)benzoate, methanesulfonamide, and potassium carbonate in acetonitrile to yield 2-[3-phenyl-2-(methylsulfonylaminocarbonyl)phenoxy]-4,6-dimethoxypyrimidine.

HERBICIDAL ACTIVITY

The plant test species used in demonstrating the herbicidal activity of compounds of this invention include cotton (*Gossypium hirsutum*), soybean (*Glycine max*), field corn (*Zea mays*), rice (*Oryza sativa*), wheat (*Triticum aestivium*), morningglory (*Ipomea lacunosa* or *Ipomea hederacea*), velvetleaf (*Abutilon theophrasti*), barnyardgrass (*Echinochloa crusgalli*), green foxtail (*Setaria viridis*), Johnsongrass (*Sorghum halepense*), and wild mustard (*Brassica kaber*).

PREPARATION OF FLATS

Preemergence

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of corn, wheat, soybean, cotton, and rice are planted in five of the furrows of the first flat (the sixth furrow is left unplanted), and seeds of morningglory, wild mustard, velvetleaf, barnyardgrass, green foxtail and Johnsongrass are planted in the six furrows of the second flat. The template is again employed to firmly press the seeds into place. A topping soil of equal portions of sand and sandy loam soil is placed uniformly on top of each flat to a depth of approximately 0.5 cm.

The flats for the preemergence test were first watered and then drenched with a solution of test compound as described below. The flats were placed in a greenhouse and watered regularly at the soil surface for 21 days at which time phytotoxicity data were recorded.

Postemergence

Two flats for each rate of application for each herbicide candidate are also prepared for postemergence application. The postemergence flats are prepared in the manner as described above for preemergence flats.

The flats for the postemergence test were placed in a greenhouse and watered for 8–10 days after which the foliage of the emerged test plants was sprayed with a solution of the test compound. After spraying, the foliage was kept dry for 24 hours and then watered regularly for 21 days after which phytotoxicity data were recorded.

APPLICATION OF HERBICIDES

In both the preemergence and postemergence tests, the candidate herbicides were applied as aqueous acetone solutions at rates equivalent to 8.0 kilograms/hectare (kg/ha) and submultiples thereof, i.e., 4.0 kg/ha, 2.0 kg/ha, and so on. Preemergence applications were made as soil drenches using 100 mL of test solution of appropriate concentration for each of the two flats/compounds. Postemergence applications were made as foliar sprays using 5 mL of test solution for each of the two flats.

Preparation of Test Solutions

For flats of the size described above, an application rate of 8.0 kg/ha of test compound is equivalent to 0.025 gram/flat. A stock solution of 0.2 gram of test compound in 40 mL of acetone containing 0.5% v/v of sorbitan monolaurate emulsifier/solubilizer was prepared. For the 8.0 kg/ha preemergence test, 10 mL of the stock solution was diluted with water to give 200 mL of test solution for application as a soil drench to both flats, 100 mL/flat. For the 8.0 kg/ha postemergence test, 10 mL of the stock solution was used undiluted as a spray, 5 mL/flat. The remaining 20 mL of stock solution was diluted with an equal volume of acetone-emulsifier to give 40 mL of a second stock solution, containing 0.1 gram of test compound, and the process above repeated, i.e., 20 mL of the solution being used for the 4.0 kg/ha application rate, and 20 mL for the preparation of lower rate test solutions by the same process.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate | Moderate injury, | Deficient weed |

-continued

Herbicide Rating System

| Rating Percent Control | Description of Main Categories | Crop Description | Weed Description |
|---|---|---|---|
| | effect | crop usually recovers | control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Contol somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, 1.0 part of sodium lignosulfonate, and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate 2% powdered sodium lignosulfonate 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

| Cmpd No. | Q | R | $R^1$ | $R^2$ | A | G |
|---|---|---|---|---|---|---|
| 1 | H | —OCH$_3$ | —OCH$_3$ | —CH$_3$ | O | —CH— |
| 2 | Cl | —OCH$_3$ | —OCH$_3$ | —CH$_3$ | O | —CH— |
| 3 | F | —OCH$_3$ | —OCH$_3$ | —CH$_3$ | O | —CH— |
| 4 | Cl | —OCH$_3$ | —OCH$_3$ | —CF$_3$ | O | —CH— |
| 5 | H | —OCH$_3$ | —OCH$_3$ | —C$_2$H$_5$ | O | —CH— |
| 6 | Cl | —OCH$_3$ | —OCH$_3$ | —C$_2$H$_5$ | O | —CH— |
| 7 | Cl | —OCH$_3$ | —OCH$_3$ | —CH$_2$CF$_3$ | O | —CH— |
| 8 | Cl | —OCH$_3$ | —OCH$_3$ | —C$_3$H$_7$ | O | —CH— |
| 9 | H | —OCH$_3$ | —OCH$_3$ | —CH(CH$_3$)$_2$ | O | —CH— |
| 10 | Cl | —OCH$_3$ | —OCH$_3$ | —CH(CH$_3$)$_2$ | O | —CH— |
| 11 | Cl | —OCH$_3$ | —OCH$_3$ | —CH$_2$CH=CH$_2$ | O | —CH— |
| 12 | Cl | —OCH$_3$ | —OCH$_3$ | —C$_4$H$_9$ | O | —CH— |
| 13 | Cl | —OCH$_3$ | —OCH$_3$ | 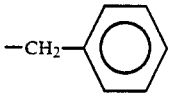 | O | —CH— |
| 14 | Cl | —OCH$_3$ | —OCH$_3$ |  | O | —CH— |
| 15 | Cl | —OCH$_3$ | —OCH$_3$ | —CH$_2$SO$_2$CH$_3$ | O | —CH— |
| 16 | H | —OCH$_3$ | —OCH$_3$ | 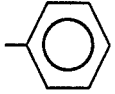 | O | —CH— |
| 17 | Cl | —OCH$_3$ | —OCH$_3$ | 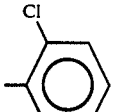 | O | —CH— |
| 18 | H | —OCH$_3$ | —OCH$_3$ | 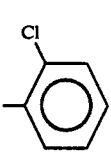 | O | —CH— |
| 19 | Cl | —OCH$_3$ | —OCH$_3$ |  | O | —CH— |
| 20 | Cl | —OCH$_3$ | —OCH$_3$ |  | O | —CH— |
| 21 | Cl | —OCH$_3$ | —OCH$_3$ |  | O | —CH— |

TABLE 1-continued

Structure:

$$\text{Q-C}_6\text{H}_3(\text{A-pyrimidine with R, R}^1\text{, G})\text{-C(=O)-NHSO}_2\text{R}^2$$

| Cmpd No. | Q | R | $R^1$ | $R^2$ | A | G |
|---|---|---|---|---|---|---|
| 22 | Cl | —OCH$_3$ | —OCH$_3$ | 2-F-phenyl | O | —CH— |
| 23 | Cl | —OCH$_3$ | —OCH$_3$ | 2-CH$_3$-phenyl | O | —CH— |
| 24 | Cl | —OCH$_3$ | —OCH$_3$ | 2-OCH$_3$-phenyl | O | —CH— |
| 25 | Cl | —OCH$_3$ | —OCH$_3$ | 4-OCH$_3$-phenyl | O | —CH— |
| 26 | Cl | —OCH$_3$ | —OCH$_3$ | 2-CN-phenyl | O | —CH— |
| 27 | Cl | —OCH$_3$ | —OCH$_3$ | 2-NO$_2$-phenyl | O | —CH— |
| 28 | Cl | —OCH$_3$ | —OCH$_3$ | 2-OCH$_3$-4-Cl-phenyl | O | —CH— |
| 29 | H | —OCH$_3$ | —OCH$_3$ | 2-pyridyl | O | —CH— |
| 30 | Cl | —OCH$_3$ | —OCH$_3$ | 3-pyridyl | O | —CH— |
| 31 | Cl | —OCH$_3$ | —OCH$_3$ | 1,3-dimethylpyrazol-4-yl | O | —CH— |
| 32 | Cl | —OCH$_3$ | —OCH$_3$ | —CH$_2$(CH$_2$)$_2$CF$_3$ | O | —CH— |

TABLE 1-continued

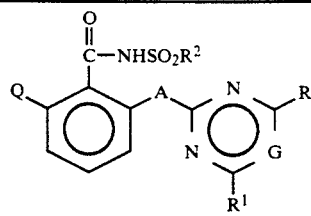

| Cmpd No. | Q | R | R$^1$ | R$^2$ | A | G |
|---|---|---|---|---|---|---|
| 33 | Cl | —OCH$_3$ | —OCH$_3$ | (cyclohexyl) | O | —CH— |
| 34 | Cl | —OCH$_3$ | —OCH$_3$ | CH$_2$CH$_2$CN | O | —CH— |
| 35 | Cl | —OCH$_3$ | —OCH$_3$ | (cyclopropyl) | O | —CH— |
| 36 | Cl | —OCH$_3$ | —OCH$_3$ | CH$_2$(CH$_2$)$_3$CH$_3$ | O | —CH— |
| 37 | Cl | —OCH$_3$ | —OCH$_3$ | CH$_2$CH$_2$OCH$_3$ | O | —CH— |
| 38 | Cl | —OCH$_3$ | —OCH$_3$ | —CH$_3$ | O | —N— |
| 39 | Cl | —OCH$_3$ | —OCH$_3$ | —CH$_3$ | NH | —CH— |
| 40 | Cl | —OCH$_3$ | —OCH$_3$ | —CH$_3$ | S | —CH— |
| 41 | (tolyl) | —OCH$_3$ | —OCH$_3$ | —CH$_3$ | O | —CH— |

TABLE 2

Identifying Properties

| Compound No. | M.P. (°C.) | Empirical Formula |
|---|---|---|
| 1 | 127-131 | C$_{14}$H$_{15}$N$_3$O$_6$S |
| 2 | 168 | C$_{14}$H$_{14}$ClN$_3$O$_6$S |
| 3 | 162-165 | C$_{14}$H$_{14}$FN$_3$O$_6$S |
| 4 | foam | C$_{14}$H$_{11}$ClF$_3$N$_3$O$_6$S |
| 5 | 112-114 | C$_{15}$H$_{17}$N$_3$O$_6$S |
| 6 | 157-158 | C$_{15}$H$_{16}$ClN$_3$O$_6$S |
| 7 | 179-182 | C$_{15}$H$_{13}$ClF$_3$N$_3$O$_6$S |
| 8 | 153-154 | C$_{16}$H$_{18}$ClN$_3$O$_6$S |
| 9 | 128-130 | C$_{16}$H$_{19}$N$_3$O$_6$S |
| 10 | 150-152 | C$_{16}$H$_{18}$ClN$_3$O$_6$S |
| 11 | 149-151 | C$_{16}$H$_{16}$ClN$_3$O$_6$S |
| 12 | 155-156 | C$_{17}$H$_{20}$ClN$_3$O$_6$S |
| 13 | 152-155 | C$_{18}$H$_{20}$ClN$_3$O$_6$S |
| 14 | 189-191 | C$_{20}$H$_{18}$ClN$_3$O$_6$S |
| 15 | 194-197 | C$_{15}$H$_{16}$ClN$_3$O$_8$S$_2$ |
| 16 | 134-144 | C$_{19}$H$_{17}$N$_3$O$_6$S$_2$ |
| 17 | 181-183 | C$_{19}$H$_{16}$ClN$_3$O$_6$S |
| 18 | 153-156 | C$_{19}$H$_{16}$ClN$_3$O$_6$S |
| 19 | 121-126 | C$_{19}$H$_{15}$Cl$_2$N$_3$O$_6$S |
| 20 | 189-192 | C$_{19}$H$_{15}$Cl$_2$N$_3$O$_6$S |
| 21 | 178-181 | C$_{19}$H$_{15}$Cl$_2$N$_3$O$_6$S |
| 22 | 139-169 | C$_{19}$H$_{15}$ClFN$_3$O$_6$S |
| 23 | 151-154 | C$_{20}$H$_{18}$ClN$_3$O$_6$S |
| 24 | 190-193 | C$_{20}$H$_{18}$ClN$_3$O$_7$S |
| 25 | 160-172 | C$_{20}$H$_{18}$ClN$_3$O$_7$S |
| 26 | 205-207 | C$_{20}$H$_{15}$ClN$_4$O$_6$S |
| 27 | 151-153 | C$_{19}$H$_{15}$ClN$_4$O$_8$S |
| 28 | 173-176 | C$_{20}$H$_{17}$Cl$_2$N$_3$O$_7$S |
| 29 | — | C$_{18}$H$_{16}$N$_4$O$_6$S |
| 30 | 202-205 | C$_{18}$H$_{15}$ClN$_4$O$_6$S |
| 31 | 155-156 | C$_{19}$H$_{18}$ClN$_5$O$_6$S |
| 32 | 180-184 | C$_{17}$H$_{17}$ClF$_3$N$_3$O$_6$S |
| 33 | 165-168 | C$_{19}$H$_{22}$ClN$_3$O$_6$S |
| 34 | 166-169 | C$_{16}$H$_{15}$ClN$_4$O$_6$S |
| 35 | 173-174 | C$_{16}$H$_{16}$ClN$_3$O$_6$S |
| 36 | 131-133 | C$_{18}$H$_{22}$ClN$_3$O$_6$S |
| 37 | 154-156 | C$_{16}$H$_{18}$ClN$_3$O$_7$S |
| 38 | — | C$_{13}$H$_{13}$ClN$_4$O$_6$S |
| 39 | — | C$_{14}$H$_{15}$ClN$_4$O$_5$S |
| 40 | — | C$_{14}$H$_{14}$ClN$_3$O$_5$S |
| 41 | — | C$_{20}$H$_{19}$N$_3$O$_6$S |

TABLE 3

Preemergence Herbicidal Activity

| Compound No. | 1 | 2 | 3 | 4 | 6 | 8 | 9 |
|---|---|---|---|---|---|---|---|
| Rate (kg/ha) | 2.0 | 0.5 | 0.5 | 1.0 | 1.0 | 0.25 | 2.0 |
| Species | % C | % C | % C | % C | % C | % C | % C |
| Cotton | 30 | 50 | 30 | 15 | 80 | 20 | 70 |
| Soybean | 5 | 95 | 40 | 0 | 95 | 70 | 60 |
| Corn | 90 | 100 | 95 | 0 | 100 | 95 | 90 |
| Rice | 100 | 95 | 80 | 5 | 95 | 50 | 95 |
| Wheat | 30 | 80 | 20 | 0 | 70 | 15 | 60 |
| Morningglory | 80 | 80 | 85 | 10 | 95 | 85 | 85 |
| Wild Mustard | 95 | 90 | 100 | 90 | 95 | 95 | 95 |
| Velvetleaf | 80 | 90 | 85 | 0 | 95 | 90 | 80 |
| Barnyardgrass | 85 | 90 | 80 | 0 | 95 | 70 | 85 |
| Green Foxtail | 95 | 85 | 100 | 0 | 95 | 95 | 60 |
| Johnsongrass | 90 | 90 | 85 | 0 | 80 | 80 | 90 |

| Compound No. | 10 | 13 | 15 | 17 | 19 | 20 | 21 |
|---|---|---|---|---|---|---|---|
| Rate (kg/ha) | 1.0 | 0.25 | 1.0 | 1.0 | 0.5 | 0.5 | 0.5 |
| Species | % C | % C | % C | % C | % C | % C | % C |
| Cotton | 80 | 60 | 40 | 60 | 15 | 15 | 5 |
| Soybean | 60 | 15 | 95 | 95 | 90 | 95 | 40 |
| Corn | 95 | 60 | 95 | 90 | 90 | 90 | 40 |
| Rice | 95 | 30 | 90 | 85 | 80 | 90 | 30 |
| Wheat | 10 | 10 | 20 | 20 | 0 | 50 | 5 |
| Morningglory | 95 | 85 | 60 | 70 | 5 | 40 | 20 |
| Wild Mustard | 95 | 95 | 95 | 95 | 90 | 90 | 90 |
| Velvetleaf | 95 | 90 | 80 | 95 | 60 | 70 | 40 |
| Barnyardgrass | 95 | 60 | 85 | 50 | 15 | 70 | 15 |
| Green Foxtail | 100 | 5 | 95 | 70 | 0 | 30 | 0 |
| Johnsongrass | 80 | 0 | 90 | 40 | 15 | 85 | 30 |

TABLE 3-continued

Preemergence Herbicidal Activity

| Compound No. | 22 | 23 | 25 | 26 | 28 | 29 | 30 |
|---|---|---|---|---|---|---|---|
| Rate (kg/ha) | 0.5 | 1.0 | 0.5 | 1.0 | 1.0 | 1.0 | 1.0 |
| Species | % C | % C | % C | % C | % C | % C | % C |
| Cotton | 5 | 5 | 60 | 5 | 20 | 20 | 10 |
| Soybean | 70 | 50 | 95 | 95 | 70 | 5 | 50 |
| Corn | 20 | 20 | 95 | 90 | 40 | 5 | 50 |
| Rice | 80 | 70 | 85 | 90 | 70 | 5 | 5 |
| Wheat | 5 | 5 | 50 | 10 | 10 | 15 | 0 |
| Morningglory | 80 | 50 | 40 | 10 | 15 | 5 | 15 |
| Wild Mustard | 95 | 95 | 90 | 95 | 95 | 70 | 95 |
| Velvetleaf | 60 | 60 | 60 | 80 | 60 | 60 | 70 |
| Barnyardgrass | 5 | 5 | 60 | 20 | 10 | 40 | 15 |
| Green Foxtail | 5 | 5 | 0 | 50 | 50 | 50 | 10 |
| Johnsongrass | 10 | 0 | 60 | 85 | 10 | 80 | 20 |

TABLE 4

Postemergence Herbicidal Activity

| Compound No. | 2 | 3 | 4 | 6 | 8 | 9 |
|---|---|---|---|---|---|---|
| Rate (kg/ha) | 0.5 | 0.5 | 1.0 | 1.0 | 0.25 | 2.0 |
| Species | % C | % C | % C | % C | % C | % C |
| Cotton | 100 | 5 | 15 | 95 | 85 | 20 |
| Soybean | 85 | 70 | 70 | 95 | 90 | 70 |
| Corn | 100 | 70 | 70 | 100 | 90 | 95 |
| Rice | 90 | 50 | 15 | 100 | 10 | 40 |
| Wheat | 95 | 15 | 50 | 95 | 30 | 40 |
| Morningglory | 80 | 60 | 60 | 95 | 95 | 60 |
| Wild Mustard | 100 | 100 | 90 | 100 | 95 | 100 |
| Velvetleaf | 100 | 85 | 40 | 100 | 100 | 85 |
| Barnyardgrass | 80 | 40 | 20 | 95 | 30 | 50 |
| Green Foxtail | 60 | 95 | 15 | 85 | 5 | 40 |
| Johnsongrass | 90 | 50 | 15 | 85 | 30 | 50 |

| Compound No. | 10 | 13 | 15 | 17 | 19 | 20 |
|---|---|---|---|---|---|---|
| Rate (kg/ha) | 1.0 | 1.0 | 1.0 | 1.0 | 0.5 | 0.5 |
| Species | % C | % C | % C | % C | % C | % C |
| Cotton | 95 | 40 | 15 | 30 | 70 | 10 |
| Soybean | 90 | 80 | 95 | 95 | 85 | 85 |
| Corn | 100 | 80 | 100 | 90 | 90 | 95 |
| Rice | 50 | 10 | 80 | 40 | 5 | 30 |
| Wheat | 50 | 15 | 60 | 50 | 20 | 15 |
| Morningglory | 100 | 90 | 80 | 90 | 70 | 70 |
| Wild Mustard | 100 | 95 | 100 | 100 | 100 | 95 |
| Velvetleaf | 100 | 95 | 95 | 100 | 85 | 85 |
| Barnyardgrass | 95 | 30 | 85 | 50 | 30 | 40 |
| Green Foxtail | 95 | 10 | 20 | 15 | 60 | 20 |
| Johnsongrass | 90 | 10 | 80 | 60 | 80 | 80 |

| Compound No. | 21 | 22 | 23 | 25 | 26 | 28 |
|---|---|---|---|---|---|---|
| Rate (kg/ha) | 0.5 | 1.0 | 1.0 | 0.5 | 1.0 | 1.0 |
| Species | % C | % C | % C | % C | % C | % C |
| Cotton | 10 | 40 | 15 | 5 | 5 | 15 |
| Soybean | 80 | 90 | 80 | 85 | 90 | 85 |
| Corn | 90 | 95 | 70 | 95 | 100 | 60 |
| Rice | 5 | 5 | 10 | 15 | 70 | 5 |
| Wheat | 5 | 15 | 10 | 20 | 30 | 15 |
| Morningglory | 60 | 70 | 40 | 80 | 70 | 20 |
| Wild Mustard | 95 | 95 | 100 | 100 | 95 | 100 |
| Velvetleaf | 40 | 80 | 40 | 70 | 90 | 40 |
| Barnyardgrass | 30 | 15 | 10 | 40 | 60 | 20 |
| Green Foxtail | 40 | 50 | 15 | 50 | 40 | 95 |
| Johnsongrass | 50 | 70 | 40 | 80 | 70 | 60 |

We claim:

1. Compound of the formula

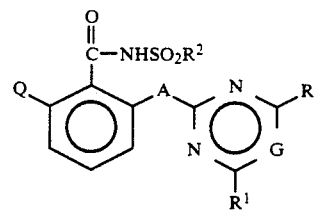

in which

A is oxygen, sulfur or $NR^3$;

G is CH;

R and $R^1$ are independently alkyl, alkoxy, haloalkoxy or alkylamino;

$R^2$ is phenyl, substituted phenyl, alkyl, cycloalkyl, haloalkyl or $-CH_2[(R^4)C(R^5)]_n-Z$;

$R^4$ and $R^5$ are independently hydrogen, alkyl, or halogen;

Z is cyano, amino, alkylamino, dialkylamino, $-NHCO_2$alkyl, alkoxy, alkylthio, alkylsulfonyl, alkenyl, alkynyl, phenyl or substituted phenyl;

n is 0 to 5;

Q is hydrogen, halogen, alkyl, alkoxy, haloalkoxy, nitro, amino, haloalkyl, alkylthio, alkylsulfonyl, phenyl, substituted phenyl, phenoxy or substituted phenoxy, or a 5- or 6-membered aromatic heterocycle selected from thiophene, furan, pyrrole, pyrazole, isoxazole, isothiazole, imidazole, oxazole, thiazole, oxadiazole, thiadiazole, triazole, tetrazole, pyridine, pyrimidine, pyrazine, pyridazine and triazine; and $R^3$ is hydrogen, alkyl, $-C(O)NH_2$ or $-C(O)$alkyl;

wherein any alkyl, alkynyl, or alkenyl moiety including the hydrocarbon moiety of any alkoxy group has less than 6 carbon atoms; any cycloalkyl group has from 3 to 7 carbon atoms; and substituted phenoxy and substituted phenyl substituents are halogen, lower alkyl, lower alkoxy, nitro, amino, lower haloalkyl, lower haloalkoxy, lower alkylthio, lower alkylsulfonyl, lower alkenyl, lower alkynyl, lower alkenyloxy or lower alkynyloxy, or two substituents taken together to form a $C_1$-$C_3$ alkylenedioxy heterocyclic ring.

2. Compound as in claim 1 in which A is oxygen and each of R and $R^1$ is methoxy.

3. Compound as in claim 2 in which Q is halogen.

4. Compound as in claim 3 in which Q is chlorine or fluorine.

5. Compound as in claim 3 in which $R^2$ is lower alkyl.

6. Compound as in claim 5 in which $R^2$ is ethyl or isopropyl.

7. An herbicidal composition containing an herbicidally effective amount of a compound of claim 1 in admixture with a suitable carrier.

8. An herbicidal composition containing an herbicidally effective amount of a compound of claim 2 in admixture with a suitable carrier.

9. An herbicidal composition containing an herbicidally effective amount of a compound of claim 5 with a suitable carrier.

10. A method for controlling unwanted plant growth which comprises applying to the locus where control is desired an herbicidally effective amount of the composition of claim 7.

11. A method for controlling unwanted plant growth which comprises applying to the locus where control is desired an herbicidally effective amount of the composition of claim 8.

12. A method for controlling unwanted plant growth which comprises applying to the locus where control is desired an herbicidally effective amount of the composition of claim 9.

13. Compound as in claim 2 in which Q is phenyl.

14. Compound as in claim 13 in which $R^2$ is lower alkyl.

15. Compound as in claim 13 in which $R^2$ is methyl.

16. A herbicidal composition containing an herbicidally effective amount of a compound of claim 14 with a suitable carrier.

17. A method for controlling unwanted plant growth which comprises applying to the locus where control is desired an herbicidally effective amount of the composition of claim 16.

* * * * *